(12) United States Patent
DeGiorgio et al.

(10) Patent No.: US 8,958,880 B2
(45) Date of Patent: Feb. 17, 2015

(54) EXTRACRANIAL IMPLANTABLE DEVICES, SYSTEMS AND METHODS FOR THE TREATMENT OF NEUROPSYCHIATRIC DISORDERS

(75) Inventors: Christopher DeGiorgio, Valencia, CA (US); Ian A. Cook, Los Angeles, CA (US); Leon Ekchian, Glendale, CA (US)

(73) Assignees: The Regents of the University of California, Oakland, CA (US); Neurosigma, Inc., Los Angeles, CA (US)

( * ) Notice: Subject to any disclaimer, the term of this patent is extended or adjusted under 35 U.S.C. 154(b) by 177 days.

(21) Appl. No.: 12/898,685

(22) Filed: Oct. 5, 2010

(65) Prior Publication Data

US 2011/0112603 A1    May 12, 2011

Related U.S. Application Data

(60) Provisional application No. 61/248,827, filed on Oct. 5, 2009, provisional application No. 61/289,829, filed on Dec. 23, 2009, provisional application No. 61/305,514, filed on Feb. 17, 2010, provisional application No. 61/354,641, filed on Jun. 14, 2010.

(51) Int. Cl.
*A61N 1/36* (2006.01)
*A61N 1/04* (2006.01)
*A61N 1/05* (2006.01)

(52) U.S. Cl.
CPC ............ *A61N 1/0456* (2013.01); *A61N 1/0476* (2013.01); *A61N 1/0492* (2013.01); *A61N 1/36025* (2013.01); *A61N 1/0529* (2013.01)
USPC ............................................. 607/45; 607/46

(58) Field of Classification Search
USPC ....................................................... 607/45, 46
See application file for complete search history.

(56) References Cited

U.S. PATENT DOCUMENTS

| 3,279,468 A | 10/1966 | Le Vine |
| 4,233,986 A | 11/1980 | Tannenbaum |
| 4,635,641 A | 1/1987 | Hoffman |

(Continued)

FOREIGN PATENT DOCUMENTS

| JP | 2008-246040 A | 10/2008 |
| JP | 4961558 B2 | 6/2012 |

(Continued)

OTHER PUBLICATIONS

DeGiorgio, C. et al., "Pilot Study of Trigeminal Nerve Stimulation (TNS) for Epilepsy: A Proof-of-Concept Trial". *Epilepsia*, 47(7): 1213-1215 (2006).

*Primary Examiner* — Joseph Dietrich
(74) *Attorney, Agent, or Firm* — Morgan, Lewis & Bockius LLP

(57) ABSTRACT

The present disclosure relates to methods, devices, and systems used for the treatment of mood, anxiety, cognitive, and behavioral disorders (collectively, neuropsychiatric disorders) via stimulation of the superficial elements of the trigeminal nerve ("TNS"). More specifically, minimally invasive systems, devices and methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerves (also referred to collectively as the superficial trigeminal nerve) are disclosed herein.

4 Claims, 9 Drawing Sheets

(56) References Cited

U.S. PATENT DOCUMENTS

| | | | |
|---|---|---|---|
| 5,514,175 | A | 5/1996 | Kim et al. |
| 5,540,734 | A | 7/1996 | Zabara |
| 6,405,079 | B1 * | 6/2002 | Ansarinia .................. 607/2 |
| 6,567,702 | B1 | 5/2003 | Nekhendzy et al. |
| 6,735,475 | B1 | 5/2004 | Whitehurst et al. |
| 6,950,707 | B2 | 9/2005 | Whitehurst |
| 6,954,668 | B1 | 10/2005 | Cuozzo |
| 7,502,652 | B2 | 3/2009 | Gaunt et al. |
| 7,734,340 | B2 | 6/2010 | De Ridder |
| 7,801,601 | B2 | 9/2010 | Maschino et al. |
| 8,380,315 | B2 | 2/2013 | DeGiorgio et al. |
| 8,428,734 | B2 | 4/2013 | Rigaux et al. |
| 8,512,715 | B2 | 8/2013 | Papay |
| 8,554,324 | B2 | 10/2013 | Brocke |
| 8,565,896 | B2 | 10/2013 | Ben-David et al. |
| 8,591,419 | B2 | 11/2013 | Tyler |
| 8,666,498 | B2 | 3/2014 | Newman |
| 8,688,220 | B2 | 4/2014 | DeGiorgio et al. |
| 8,700,164 | B2 | 4/2014 | DeGiorgio et al. |
| 2002/0077670 | A1 | 6/2002 | Archer et al. |
| 2004/0138097 | A1 | 7/2004 | Guyuron |
| 2004/0176820 | A1 | 9/2004 | Paul |
| 2005/0283198 | A1 | 12/2005 | Haubrich |
| 2006/0064140 | A1 | 3/2006 | Whitehurst et al. |
| 2006/0167500 | A1 | 7/2006 | Towe et al. |
| 2006/0173510 | A1 | 8/2006 | Besio et al. |
| 2006/0200208 | A1 | 9/2006 | Terry, Jr. et al. |
| 2006/0206165 | A1 | 9/2006 | Jaax et al. |
| 2006/0293723 | A1 | 12/2006 | Whitehurst et al. |
| 2007/0150025 | A1 | 6/2007 | Dilorenzo et al. |
| 2007/0150027 | A1 | 6/2007 | Rogers |
| 2007/0173908 | A1 | 7/2007 | Begnaud |
| 2007/0179557 | A1 | 8/2007 | Maschino et al. |
| 2007/0233194 | A1 | 10/2007 | Craig |
| 2007/0276451 | A1 | 11/2007 | Rigaux |
| 2008/0046013 | A1 | 2/2008 | Lozano |
| 2008/0103547 | A1 | 5/2008 | Okun et al. |
| 2008/0128215 | A1 | 6/2008 | Nowitz |
| 2008/0132980 | A1 | 6/2008 | Gerber et al. |
| 2008/0147141 | A1 | 6/2008 | Testerman et al. |
| 2008/0161713 | A1 | 7/2008 | Leyde et al. |
| 2008/0171929 | A1 | 7/2008 | Katims |
| 2008/0172101 | A1 | 7/2008 | Bolea et al. |
| 2008/0269716 | A1 | 10/2008 | Bonde et al. |
| 2009/0048642 | A1 | 2/2009 | Goroszeniuk |
| 2009/0210028 | A1 | 8/2009 | Rigaux et al. |
| 2009/0287035 | A1 | 11/2009 | Dietrich et al. |
| 2010/0030227 | A1 | 2/2010 | Kast et al. |
| 2010/0198282 | A1 | 8/2010 | Rogers |
| 2010/0222847 | A1 | 9/2010 | Goetz |
| 2010/0228105 | A1 | 9/2010 | Policker et al. |
| 2010/0262205 | A1 | 10/2010 | De Ridder |
| 2011/0093033 | A1 | 4/2011 | Nekhendzy |
| 2011/0106220 | A1 | 5/2011 | DeGiorgio et al. |
| 2011/0184489 | A1 | 7/2011 | Nicolelis et al. |
| 2011/0218589 | A1 | 9/2011 | DeGiorgio et al. |
| 2011/0218590 | A1 | 9/2011 | DeGiorgio et al. |
| 2011/0282129 | A1 | 11/2011 | Rigaux |
| 2012/0203301 | A1 | 8/2012 | Cameron et al. |
| 2013/0158626 | A1 | 6/2013 | DeGiorgio et al. |
| 2014/0046407 | A1 | 2/2014 | Ben-Ezra et al. |
| 2014/0081353 | A1 | 3/2014 | Cook et al. |
| 2014/0081369 | A1 | 3/2014 | Sosa et al. |

FOREIGN PATENT DOCUMENTS

| | | |
|---|---|---|
| JP | 2003-339884 A | 12/2013 |
| RU | 2086227 C1 | 8/1997 |
| RU | 2185092 C1 | 7/2002 |
| SU | 1718976 A1 | 3/1992 |
| WO | WO 2006/044793 A2 | 4/2006 |
| WO | WO 2007/136726 | 11/2007 |
| WO | WO 2009/158389 | 12/2009 |
| WO | WO 2011/044173 | 4/2011 |
| WO | WO 2011/044176 | 4/2011 |
| WO | WO 2011/044178 | 4/2011 |
| WO | WO 2011/044179 | 4/2011 |
| WO | WO 2012/075192 A2 | 6/2012 |
| WO | WO 2012/082960 | 6/2012 |
| WO | WO 2012/082961 | 6/2012 |
| WO | WO 2013/104552 A1 | 7/2013 |
| WO | WO 2013/152316 A1 | 10/2013 |

* cited by examiner

| PULSE DURATION (Usec) | 150us | 200us | 250us |
|---|---|---|---|
| mA'S RECORDED (MAX TOLERATED SETTINGS) | 7.92 | 5.94 | 5.72 |
| ELECTRODE RADIUS(cm) (1.25" DIAMETER ROUND ELECTRODES) | 1.59cm | 1.59cm | 1.59cm |
| SURFACE AREA cm | 7.92cm$^2$ | 7.92cm$^2$ | 7.92cm$^2$ |
| CURRENT DENSITY mA/cm$^2$ | 1 | .75 | .72 |
| MAXIMUM SAFE CURRENT DENSITY AT STIMULATING ELECTRODE mA/cm$^2$ | 25 | 25 | 25 |
| CHARGE DENSITY (A)(pulse)/cm$^2$ =uC/cm$^2$ AT STIMULATING ELECTRODE | .15 | .15 | 0.18 |
| MAXIMUM SAFE CHARGE DENSITY (uC/cm$^2$) AT BRAIN | 10 | 10 | 10 |

FIG.6

EXTRACRANIAL IMPLANTABLE DEVICES, SYSTEMS AND METHODS FOR THE TREATMENT OF NEUROPSYCHIATRIC DISORDERS

CROSS REFERENCE TO RELATED APPLICATIONS

This application claims the benefit of priority under 35 U.S.C. §119(e) to the following applications: U.S. Application No. 61/248,827, entitled "Devices and Methods for Treatment of Psychiatric Disorders," filed Oct. 5, 2009; U.S. Application No. 61/289,829, entitled "Extracranial Implantable Devices, Systems and Methods for Treatment of Neuropsychiatric Disorders," filed Dec. 23, 2009; U.S. Application No. 61/305,514, entitled "Systems, Devices and Methods for Treatment of Neurological Disorders and Conditions," filed Feb. 17, 2010; and U.S. Application No. 61/354,641, entitled "Extracranial Implantable Devices, Systems and Methods for Treatment of Neurological Disorders," filed Jun. 14, 2010, and each of the above applications is hereby incorporated by reference as though fully set forth herein.

This application is also related to the following copending applications: U.S. application Ser. No. 12/898,686, entitled "Devices, Systems and Methods for Treatment of Neuropsychiatric Disorders," filed on even date herewith U.S. application Ser. No. 12/898,675, entitled "Systems, Devices and Methods for the Treatment of Neurological Disorders and Conditions," filed on even date herewith U.S. application Ser. No. 12/898,696, entitled "Extracranial Implantable Devices, Systems and Methods for Treatment of Neurological Disorders," filed on even date herewith and each of the above applications is hereby incorporated by reference as though fully set forth herein.

FIELD

The present disclosure generally relates to implantable neurostimulator systems, devices and methods of using the same and more particularly relates to implantable neurostimulator systems, devices and methods including at least one implantable electrode for treating neuropsychiatric disorders by stimulating superficial, cutaneous elements of cranial nerve(s).

BACKGROUND

Psychiatric or neuropsychiatric disorders, for example depressive disorders (DD), sometimes referred to as depression, or anxiety disorders, are traditionally treated with pharmacotherapy and psychotherapy. However, a substantial percentage of patients with these and other conditions do not recover despite multiple trials of treatment. Traditionally, brain stimulation has been a primary treatment alternative, and electroconvulsive therapy (ECT, or "electroshock" therapy) has been the dominant brain stimulation approach since the first part of the 20th century. ECT carries risks of memory and other cognitive side effects, considerable cost, and risks of anesthesia. Two implantable approaches have also been described: deep brain stimulation (DBS), in which electrodes are implanted directly within the brain, and vagus nerve stimulation (VNS) in which stimulating electrodes are implanted on the vagus nerve in the neck. While the U.S. Food and Drug Administration (FDA) have approved systems for deep brain stimulation for the treatment of Parkinson's disease, DBS is presently an experimental intervention for other neuropsychiatric conditions. The risks of DBS include infection, hemorrhage, and injury to deep brain structures. In reports of clinical studies with VNS, many of the patients who undergo VNS treatments do not achieve remission, and there is no reliable predictor of good outcomes from the implanted VNS device.

SUMMARY

One aspect of the subject matter of the present disclosure addresses the aforementioned needs by providing a method of treating psychiatric disorders and systems and devices configured to stimulate the ophthalmic (supra-orbital), infraorbital, and mentalis branches of the trigeminal nerve, located in the face, and more specifically, by providing a method of treating psychiatric disorders using trigeminal nerve stimulation (TNS) with minimally invasive, implantable and easy-to-use devices and systems.

In another aspect of the present disclosure, an implantable electrode assembly configured for trigeminal nerve stimulation is provided.

In yet another aspect of the present disclosure, a method of treating psychiatric disorders using the disclosed implantable electrode assembly is provided.

In one aspect, a system for trigeminal nerve stimulation for treatment of a neuropsychiatric disorder is disclosed. In one embodiment, the system includes: a pulse generator; and a subcutaneous electrode assembly in electrical communication with the pulse generator. The assembly includes: a first electrode comprising at least one contact configured for subcutaneous placement at a first region of the patient's face, wherein the first electrode is configured to be implanted in proximity to, adjacent to or in contact with at least one branch of the trigeminal nerve for treatment of a neuropsychiatric disorder by trigeminal nerve stimulation, wherein the system is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the system further includes a second electrode comprising at least one contact configured for subcutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the first electrode and the second electrode are configured for implantation in proximity to, adjacent to or in contact with a same branch of the trigeminal nerve. In one embodiment, the first electrode and the second electrode are configured for implantation in proximity to, adjacent to or in contact with a different branch of the trigeminal nerve. The system may further include a wire operably connecting the pulse generator and the subcutaneous electrode assembly. The system may further include a regulating device configured to regulate the maximum charge balanced output current below approximately 30-50 mA. The neuropsychiatric disorder is selected from the group consisting of: mood disorder, cognitive disorder, behavioral disorder and anxiety disorder. In one embodiment, the pulse generator is configured to apply electrical signals at a frequency between approximately 20 and 300 Hertz, at a pulse duration between approximately 50 and 500 microseconds, at an output current density of not greater than approximately 25 mA/cm$^2$ and an output charge density of not greater than approximately 10 microCoulomb/cm$^2$ at the cerebral cortex.

In one aspect, a subcutaneous electrode assembly for trigeminal nerve stimulation for treatment of a neuropsychiatric disorder is disclosed. In one embodiment, the assembly includes a first electrode comprising at least one contact configured for subcutaneous placement at a first region of the patient's face, wherein the first electrode is configured to be implanted in proximity to, adjacent to or in contact with at least one branch of the trigeminal nerve for treatment of a neuropsychiatric disorder by trigeminal nerve stimulation, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the assembly may further include a second electrode comprising at least one contact configured for subcutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In some embodiments, the first electrode and the second electrode are configured for implantation in proximity to, adjacent to or in contact with a same branch of the trigeminal nerve. In some embodiments, the first electrode and the second electrode are configured for implantation in proximity to, adjacent to or in contact with a different branch of the trigeminal nerve. The neuropsychiatric disorder is selected from the group consisting of: mood disorder, cognitive disorder, behavioral disorder and anxiety disorder.

In another aspect, a method for treating a neuropsychiatric disorder by trigeminal nerve stimulation is disclosed. In one embodiment, the method includes implanting an electrode assembly in a patient, the subcutaneous electrode assembly comprising: a first electrode comprising at least one contact configured for subcutaneous placement at a first region of the patient's face, wherein the first electrode is configured to be implanted in proximity to, adjacent to or in contact with at least one branch of the trigeminal nerve for treatment of a neuropsychiatric disorder by trigeminal nerve stimulation, wherein the assembly is configured for minimal current penetration into a brain of a patient, and wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve; and applying electrical signals to the electrode assembly at specified operational parameters to treat a neuropsychiatric disorder. The method may further include the assembly comprising a second electrode comprising at least one contact configured for subcutaneous placement at a second region of the patient's face, wherein the second electrode is configured to be implanted in proximity to, adjacent to or in contact with at least one branch of the trigeminal nerve, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, nasal nerve, and auriculotemporal nerve. In one embodiment, the step of applying electrical signals comprises applying electrical signals at a frequency between approximately 20 and 300 Hertz, at a current of 0.05 to 5 milliamperes (mA) and at a pulse duration of less than or equal to 500 microseconds. In one embodiment, the step of applying electrical signals comprises applying electrical signals at a frequency between approximately 20 and 300 Hertz, at a pulse duration between approximately 50 and 500 microseconds, at an output current density of not greater than approximately 25 mA/cm$^2$ and a charge density of not greater than approximately 10 microCoulomb/cm$^2$ at the cerebral cortex. The neuropsychiatric disorder is selected from the group consisting of: mood disorder, cognitive disorder, behavioral disorder and anxiety disorder.

In another aspect, a kit for trigeminal nerve stimulation for treatment of a neuropsychiatric disorder is disclosed. In one embodiment, the kit includes the subcutaneous electrode assembly according to claim 1; and instructions for implanting the electrode assembly in a patient for treatment of a neuropsychiatric disorder. In one embodiment, the kit may further include a pulse generator; and instructions for applying electrical signals to the electrode assembly for treatment of a neuropsychiatric disorder.

BRIEF DESCRIPTION OF THE DRAWINGS

The present disclosure, both as to its organization and manner of operation, may be understood by reference to the following description, taken in connection with the accompanying drawings, in which:

FIG. 6 summarizes current, charge, current density and charge density in a subject exposed to transcutaneous stimulation of the supraorbital nerve.

DETAILED DESCRIPTION

Figures 1A, 1B:
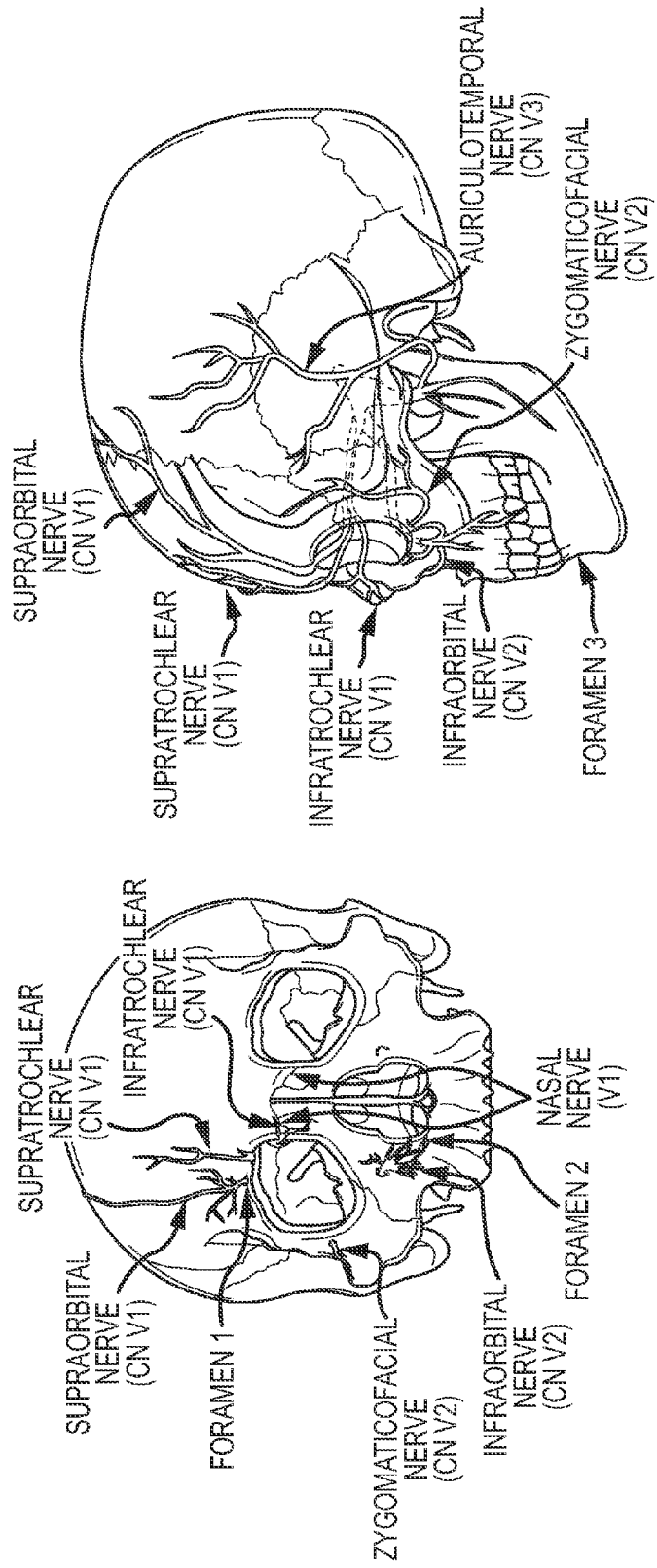
FIGS. 1A and 1B illustrate the location of several branches (nerves) of the trigeminal nerve and the location of the major foramina for the superficial branches of the trigeminal nerve.

The present disclosure relates to methods, devices, and systems used for the treatment of mood, anxiety, cognitive, and behavioral disorders (collectively, neuropsychiatric disorders) via stimulation of the superficial elements of the trigeminal nerve ("TNS"). More specifically, minimally invasive systems, devices and methods of stimulation of the superficial branches of the trigeminal nerve located extracranially in the face, namely the supraorbital, supratrochlear, infraorbital, auriculotemporal, zygomaticotemporal, zygomaticoorbital, zygomaticofacial, nasal and mentalis nerves (also referred to collectively as the superficial trigeminal nerve) are disclosed herein. Methods for the treatment of mood disorders and other neuropsychiatric disorders by sTNS (subcutaneous trigeminal nerve stimulation) are also provided. Systems and devices configured for therapeutic stimulation of the branches of the trigeminal nerves, such as the superficial trigeminal nerve, and their methods of application are also described.

The systems, devices and methods disclosed herein provide a less invasive form of neurostimulation to treat a variety of neuropsychiatric disorders including, but not limited to, mood, anxiety, cognitive, and behavioral disorders. More specifically, an implantable or subcutaneous electrode assembly and a system comprising the same configured for trigeminal nerve stimulation are disclosed herein. As described in more detail below, electrodes are not placed within the brain or near critical structures like the vagus nerve, carotid artery, or jugular vein. The electrodes are also not directly or physically attached or anchored to the nerve (e.g. by suturing), which requires intracranial invasion and may cause a spinal fluid leak, infection, nerve damage and/or severe pain. Instead, subcutaneous electrodes (or an electrode assembly) are placed at or near a region of a patient's face or cranium that is in proximity to, adjacent to, in contact with, or distal to the trigeminal nerve (or the relevant branch(es) thereof) by attaching to subcutaneous or connective tissues above the periosteum or pericranium (a membrane that lines the outer surface of the skull) and below the epidermis (the outermost layer of skin). The nerve is stimulated at operational parameters within a predefined range and that may be further refined by factors such as patient history, disorder to be treated, or individual sensitivity to the stimulation. The electrode assembly placement as described herein does not require intracranial invasion (i.e. implantation below the skull) thereby reducing the risks of a spinal fluid leak and infection. In some embodiments, the electrode assembly may be placed or otherwise configured to stimulate the smaller branches of the trigeminal nerve. That is, the assembly is placed further away from the brain and the main branch of the nerve. Surprisingly, placement of the assembly further away from the brain and the main branch of the nerve is believed to be as efficacious as direct attachment to the main branch of the nerve and may provide increased safety for the patient.

Some brain stimulation methods aim to generate currents in large volumes of the cortex and treat the brain as a bulk conductor, for example, ECT (electroconvulsive therapy) at the whole-lobe level and rTMS (repetitive transcranial magnetic stimulation) at the large regional level (i.e. dorsolateral prefrontal cortex). Additionally, deep brain stimulation is generally predicated on stimulation of small but regional volumes that lead to discharges in a very large number of cells. The systems, devices and methods of the present disclosure send minimal, if any, current into the brain; instead, signals are sent into the brain in order to modulate the activity of relevant neuroanatomical structures. Without wishing to be bound by any particular theory, the electrical pulses generate signals in the cutaneous branches of the trigeminal nerve and the electric fields are generally confined to the skin tissue and there is minimal, if any, leakage into the brain. These electrical pulses trigger a cascade of change in neuronal signaling events that involve very limited and precise recruitment of specific networks of neurons. The neuroanatomic pathways allow targeted modulation of activity in areas involved in mood disorders, anxiety disorders, and other neuropsychiatric conditions (locus coeruleus, anterior cingulate, insula, amygdala, and other cortical and subcortical structures). Thus, the systems, devices and methods as disclosed herein utilize the brain's existing infrastructure to transmit signals to the targets of interest. In the context of this disclosure minimal current penetration means (1) a charge density of approximately 0 uC/cm2 at the cerebral cortex, or (2) calculated, measured, or modeled charge densities below the following thresholds at the cerebral cortex: (a) at currents, charge densities, or charge per phase not likely to cause activation of pyramidal neurons and axons; and (b) to prevent brain injury, a charge density of less than 10 uC/cm2 in one embodiment, and, in other embodiments, a charge density of less than 0.001 to 0.1 uC/cm2, and at combinations of charge density and charge per phase not known to cause brain injury. In some embodiments, a lower charge density may be used when the central nervous system of an individual patient is sufficiently sensitive to lower levels of stimulation that the lower level will still permit clinical benefit to accrue.

The following description is provided to enable any person skilled in the art to make and use the subject matter of this disclosure. Various modifications, however, will remain readily apparent to those skilled in the art, since the general principles of the disclosed subject matter have been defined herein specifically to describe: (1) methods of treating neuropsychiatric disorders by trigeminal nerve stimulation, (2) a system and an implantable electrode assembly configured for trigeminal nerve stimulation; and (3) methods of treating neuropsychiatric disorders using such electrode assembly.

With reference to FIGS. 1A and 1B, the trigeminal nerve is the largest cranial nerve, and has extensive connections with the brainstem and other brain structures. The trigeminal nerve has three major sensory branches over the face, all of which are bilateral, and highly accessible. The supraorbital nerve, or ophthalmic nerve, is frequently referred to as the $V_1$ division. The infraorbital branch or maxillary nerve is commonly referred to as the $V_2$ division. The mentalis branch of the mandibular nerve is referred to as the $V_3$ division. The supraorbital nerve supplies sensory information about pain, temperature, and light touch to the skin of the forehead, the upper eyelid, the anterior part of the nose, and the eye. The infraorbital branch supplies sensory information about pain, temperature, and light touch sensation to the lower eyelid, cheek, and upper lip. The mentalis branch supplies similar sensory modalities to the skin of the lower face (e.g. jaw and tongue) and lips.

These branches exit the skull through three foramina, as shown in FIGS. 1A and 1B. The supraorbital nerve or ophthalmic nerve exits at foramen 1, approximately 2.1-2.6 cm from the nasal midline (in adults), and is located immediately above the orbital ridge that is located below the eyebrow. The infraorbital branch or maxillary nerve exits at foramen 2, approximately 2.4-3.0 cm from the nasal midline (in adults) and the mentalis nerve exits at foramen 3, approximately 2.0-2.3 cm from the nasal midline (in adults). Other sensory branches, including the zygomaticofacial, zygomaticoorbital, zygomaticotemporal, and auriculotemporal, arise from other foramina.

Fibers from the three major branches join together to form the trigeminal ganglion. From there, fibers ascend into the brainstem at the level of the pons to synapse with the main sensory nucleus of the pons, the mesencephalic nucleus of V, and the spinal nucleus and tract of V. Pain fibers descend in the spinal nucleus and tract of V, and then ascend to the ventral posterior medial nucleus (VPM) of the thalamus, and then project to the cerebral cortex. Light touch sensory fibers are large myelinated fibers, which ascend to the ventral posterior lateral (VPL) nucleus of the thalamus, and also project to the cerebral cortex. Afferent sensory fibers project from the trigeminal nuclei to the thalamus and the cerebral cortex.

The trigeminal nucleus has reciprocal projections to the nucleus tractus solitarius (NTS), the locus coeruleus, and the vagus nerve. The NTS receives afferents from the vagus nerve and trigeminal nerve. NTS integrates input from multiple sources, and projects to structures in the brainstem and forebrain, including the locus coeruleus.

The locus coeruleus is a paired nuclear structure in the dorsal pons, and is located just beneath the floor of the fourth ventricle. The locus coeruleus has extensive axonal projections to a broad number of brainstem, sub-cortical and cortical structures, and is an important part of the reticular activating system. The locus coeruleus is a core part of the brainstem noradrenergic pathway, and produces the neurotransmitter norepinephrine. Norepinephrine plays a key role in attention, alertness, blood pressure and heart rate regulation, anxiety, and mood.

While not wishing to be bound by any particular theory, in certain embodiments, the connections between the trigeminal nerve and the locus coeruleus, thalamus, amygdala, anterior cingulate, and other central nervous system structures as described above may be relevant to a potential role of the trigeminal nerve in numerous neuropsychiatric disorders, including mood (such as depression), anxiety (such as post-traumatic stress disorder), and others, as may be apparent to one skilled in the art. Thus, subcutaneous stimulation of the trigeminal nerve could be effective in the treatment of neuropsychiatric disorders.

For a discussion of certain embodiments of methods, systems and devices using subcutaneous electrodes according to aspects of the present disclosure, reference is now made to FIGS. 2A-4, which show various embodiments of the systems and devices that may be used for the subcutaneous stimulation of the superficial branches of the trigeminal nerve and methods of using the same.

According to one aspect of the present disclosure, a method of treating neuropsychiatric disorders using trigeminal nerve stimulation ("TNS") is provided. In some embodiments, the method of treating these disorders by stimulating superficial branches of the trigeminal nerve comprises implanting electrodes adjacent to, in proximity to, or distal to at least one of the three paired foramina or superficial branches of the trigeminal nerves in the face (FIGS. 1A and 1B), and stimulating the electrodes using a neurostimulator for a fixed time at specified operational parameters. The electrode assembly placement does not require intracranial invasion (i.e. implantation below the skull) because the electrode assembly is attached or otherwise anchored to subcutaneous or connective tissues located above the periosteum or pericranium and below the epidermis in order to place the electrode assembly in proximity to, adjacent to, in contact with or distal to the target nerve branch. In some embodiments, the electrode assembly may be configured to stimulate the smaller branches of the trigeminal nerve. Surprisingly, placement of the assembly further away from the brain and the main branch of the nerve is believed to be as efficacious as direct attachment or other contact with the main branch of the nerve and may provide increased safety for the patient.

Figure 2A:
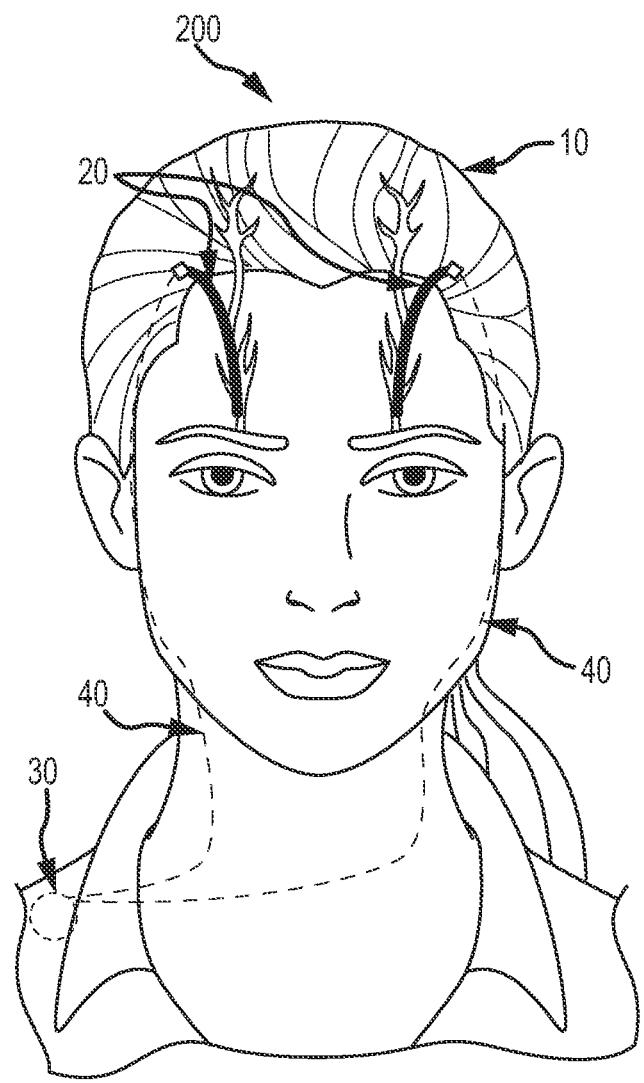
FIG. 2A shows a subject wearing an embodiment of a system for trigeminal nerve stimulation including a subcutaneous electrode assembly provided according to aspects of the present disclosure.

In one embodiment, the implanted electrodes are positioned adjacent to the foramina of the supraorbital or ophthalmic nerves (FIG. 1A, Foramen 1) since unilateral stimulation or bilateral stimulation of the trigeminal nerve is achievable by placing single or separate electrodes on the right and/or left sides. In one embodiment, the electrode assembly is configured for unilateral stimulation. In one embodiment, the electrode assembly is configured for bilateral stimulation. In some embodiments, bilateral stimulation may offer similar or better efficacy than unilateral stimulation because the function of different brain structures may not be the same on right and left (e.g. verbal expression is most commonly localized to speech centers in the left hemisphere, and injury there produces catastrophic loss of the ability to speak, while damage to the corresponding region on the right does not produce this profound loss of function, but may alter subtle functions). There may also be synergistic effects that arise with bilateral stimulation. FIG. 2A shows an example of a patient 10 who has been implanted with two separate electrodes 12 in the soft tissues of the forehead, one over each eyebrow, corresponding to the foramina of the ophthalmic nerves. In alternative embodiments, the implanted/implantable electrode(s) can be positioned adjacent to or in proximity to the infraorbital foramen (infraorbital nerves) (FIG. 1A, Foramen 2) or the mentalis foramen (mentalis nerves) (FIG. 1B, Foramen 3). In other embodiments, electrodes may be placed adjacent to, in proximity to, or in contact with the supratrochlear nerve, infratrochlear nerve, zygomaticotemporal, zygomaticofacial, zygomaticoorbital, nasal, and/or auriculotemporal nerves and/or their respective foramina. In yet other embodiments, the stimulation can be unilaterally applied near one superficial foramen of the trigeminal nerves. Unilateral stimulation or bilateral stimulation of the trigeminal nerve is achievable by placing single or separate electrodes on the right and/or left sides of the face to unilaterally apply stimulation near one superficial foramen of the trigeminal nerves. In other embodiments, the method of treating neuropsychiatric disorders comprises implanting electrodes over a plurality of superficial foramina in the face and simultaneously or asynchronously stimulating different trigeminal nerves. In other embodiments, the stimulation may take place in the cutaneous territories of branches of the trigeminal nerves, without attachment to the nerves.

In one embodiment, as can be understood from FIGS. 2A-4, a system 200 for treatment of neuropsychiatric disorders via TNS includes an electrode assembly 20, electrical cable or wire 40 and a neurostimulator or pulse generator 30.

The pulse generator may be any type of appropriate stimulating, signal generating device. In some embodiments, the pulse generator 30 may include electronic circuitry for receiving data and/or power from outside the body by inductive, radio-frequency (RF), or other electromagnetic coupling. In some embodiments, electronic circuitry includes an inductive coil for receiving and transmitting RF data and/or power, an integrated circuit (IC) chip for decoding and storing stimulation parameters and generating stimulation pulses, and additional discrete electronic components required to complete the electronic circuit functions, e.g. capacitor(s), resistor(s), transistor(s), coil(s), and the like.

In other embodiments, neurostimulator 30 may include a programmable memory for storing a set(s) of data, stimulation, and control parameters. Among other things, memory may allow stimulation and control parameters to be adjusted to settings that are safe and efficacious with minimal discomfort for each individual. Specific parameters may provide therapeutic advantages for various psychiatric disorders. For instance, some patients may respond favorably to intermittent stimulation, while others may require continuous stimulation to treat their symptoms.

In some embodiments, the neurostimulator 30 may include a power source and/or power storage device. Possible options for providing power to the system include but are not limited to: an external power source coupled to neurostimulator 30, e.g., via an RF link, a self-contained power source utilizing any suitable means of generation or storage of energy (e.g., a primary battery, a replenishable or rechargeable battery such as a lithium ion battery, an electrolytic capacitor, a supercapacitor, a kinetic generator, or the like), and if the self-contained power source is replenishable or rechargeable, means of replenishing or recharging the power source (e.g., an RF link, an optical link, a thermal link, an inductive link, or other energy-coupling link).

In some embodiments, neurostimulator 30 operates independently. In other embodiments, neurostimulator 30 operates in coordination with other implanted device(s) or other device(s) external to the patient's body. For example, a neurostimulator may communicate with other implanted neurostimulators, other implanted devices, and/or devices external to a patient's body via, e.g., an RF link, an ultrasonic link, a thermal link, an optical link, or the like. Specifically, a neurostimulator may communicate with an external remote control (e.g., patient and/or physician programmer) that is capable of sending commands and/or data to a neurostimulator and that may also be capable of receiving commands and/or data from a neurostimulator.

In one embodiment, the electrical cable or wire 40 is configured to provide a physical and electrical link between the pulse generator 30 and the electrode assembly 20. In other embodiments, the pulse generator 30 and the electrode assembly 20 communicate wirelessly (i.e. the wire 40 is not used). The system 200 and/or the electrode assembly 20 may be part of a kit. In some embodiments, the kit may also include instructions for treatment of a neuropsychiatric disorder according to a method disclosed herein.

In some embodiments, the system may include a regulation device. The regulation device is configured to be attached to the pulse generator 15 and is configured to govern the maximum charge balanced output current below approximately 30-50 mA to minimize current penetration to the brain and increase patient tolerance. The regulation device may be internally programmed to range from 0.25-5.0, 0-10, 0-15, depending on the surface area, placement, and orientation of the electrode, and whether the electrode is stimulating near or adjacent to the skull, or away from the skull, (mentalis), where current ranges may be higher or lower. Current TENS units stimulate with maximum output currents of up to 100 mA's, which result in currents which may penetrate the skull and which may not be well tolerated.

Figure 2B:
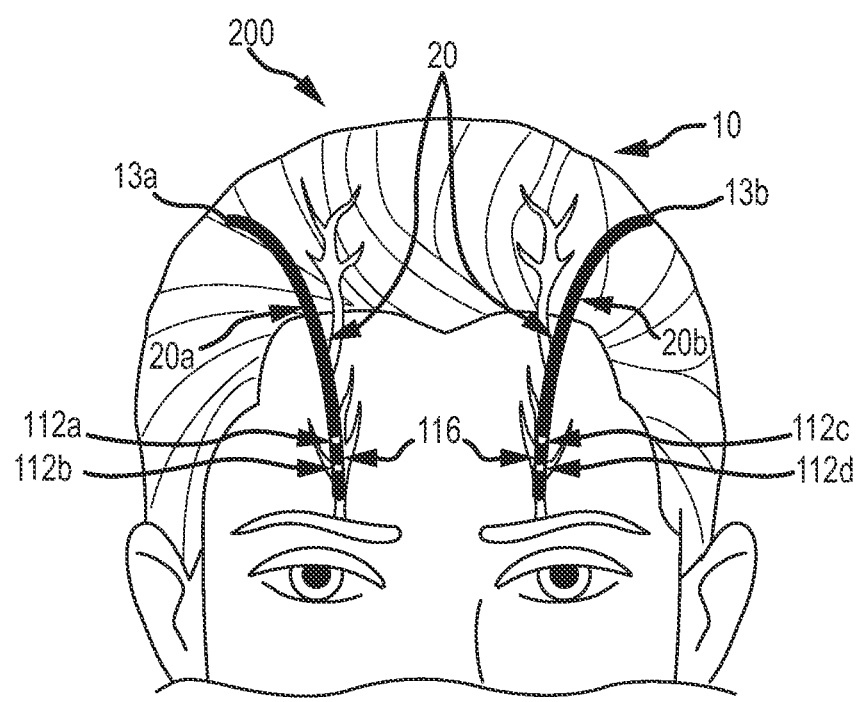
FIG. 2B is the subcutaneous electrode assembly of FIG. 2A, wherein a multicontact electrode is shown.

In one embodiment, as shown in FIGS. 2A-2B, the electrode assembly 20 is also referred to as a bilateral supraorbital electrode. The electrode assembly 20 is connectable to an implanted/implantable neurostimulator by electrical cables 40. Alternatively, the electrodes may be connectable to an external neurostimulator wirelessly, with transfer of energy across the skin by inductive coupling between a coil implanted in the patient and a coil in the external neurostimulator.

In one embodiment, as illustrated in FIG. 2B, an electrode assembly 20 may include electrodes 20a, 20b configured for the bilateral simultaneous and asynchronous stimulation of the ophthalmic nerves and other nerves as described herein. The electrodes 20a, 20b of the electrode assembly 20 comprise a first pair of contacts 112a, 112b configured for implantation in a first region of the patient's face, such as the patient's right forehead, and a second pair of contacts 112c, 112d configured for implantation in a second region of the patient's face, such as in the patient's left forehead. In other embodiments, the first and second regions of the patient's face may be on the same side of the face, e.g. the right or left side, but may be at different locations, e.g. the right forehead or the right upper face area, the right cheek area or middle face area or the right lower face area or mouth/jaw area. The electrode assembly 20 may also include an insulated region 116 or a plurality of insulated regions 116 configured to separate the individual electrode contacts. The first pair of contacts comprises a first upper contact 112a and a first lower contact 112b, while the second pair of contacts comprises a second upper contact 112c and a second lower contact 112d. The electrode assembly 20 comprises four electrodes that deliver the stimulation pulses to the nerves bilaterally. While the electrode assembly 20 is shown in FIG. 2B with only pairs of electrical contacts (112a/b, 112c/d), in other embodiments, there may be a greater or lesser number of contacts on each of the assemblies 20a and 20b.

Figure 3:
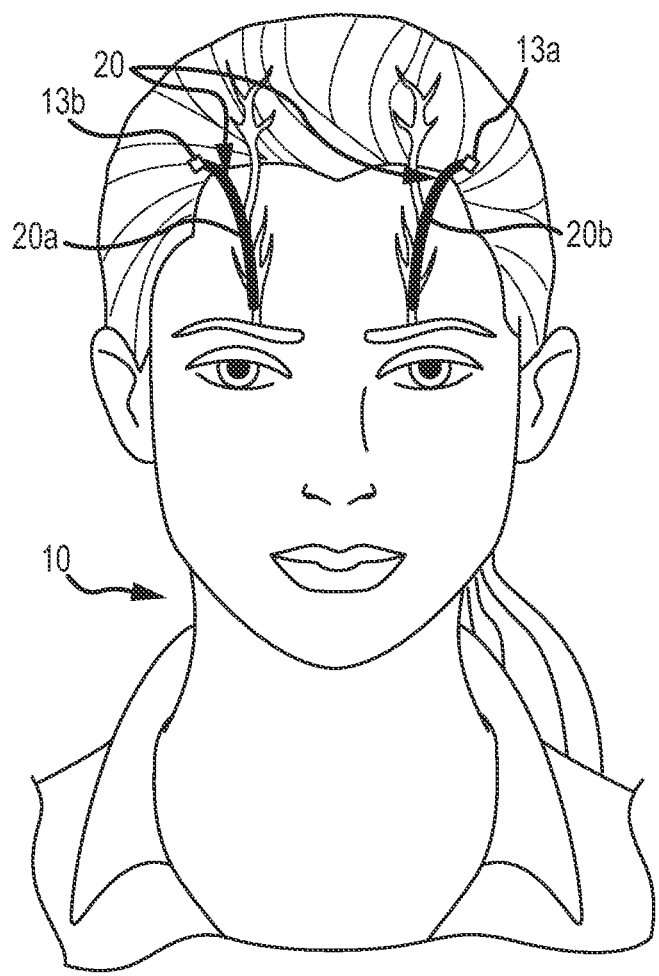
FIG. 3 depicts another embodiment of a subcutaneous electrode assembly which may be used with the system of FIG. 2A.

FIG. 3 shows another embodiment of an electrode assembly 20 that may be used in the system 200. FIG. 3 shows an example of a patient 10 who has been implanted with the electrode assembly 20, provided in accordance with the present disclosure. In one embodiment, as shown in FIG. 3, the electrode assembly may comprise two implanted electrodes 20a, 20b which are placed adjacent to the supraorbital foramina, located over the orbital ridge approximately 2.1 to 2.6 cm lateral to the nasal midline. As shown in FIG. 3, the superior ends 13a, 13b of the electrodes 20a, 20b indicate the place at which the electrodes 20 connect to leads (see FIG. 2A) for conveying the electrical stimuli from the neurostimulator (see FIG. 2A). The neurostimulator itself may be placed in a variety of locations under the skin, such as pectorally, and the leads placed under the skin of the patient to connect them.

In some embodiments, such as the embodiments shown in FIGS. 2A-3, the neurostimulation may be provided using an electrical neurostimulator at the following exemplary settings: frequency between approximately 20-150 Hz, current between approximately 0.05-20 mA, pulse duration of between approximately 50-250 microseconds, a duty cycle of 10% to 50%, for at least one hour per day. For patient comfort and low power consumption, stimulation parameters at the lower end of these ranges may be preferred. In other embodiments, different values of the operational parameters may be used. In alternative embodiments, a single implanted electrode with one or more contacts can be used.

Figure 4A:
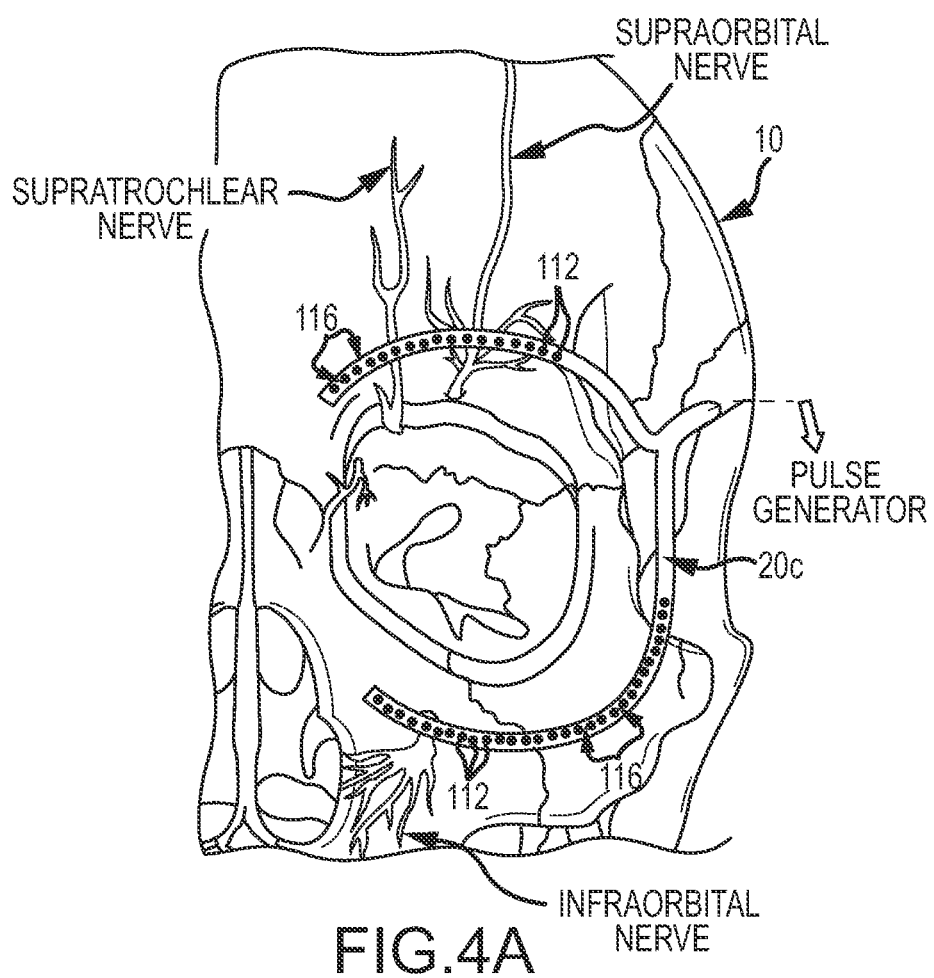
FIG. 4A depicts another embodiment of a subcutaneous electrode assembly configured for stimulation of a plurality of nerve branches which may be used with the system of FIG. 2A.

FIG. 4A depicts still another embodiment of an electrode assembly 20 that may be used in the system 200. In some embodiments, as shown in FIG. 4A, the electrode assembly 20 may comprise a multicontact electrode 20c with a plurality of contacts 112 and a plurality of insulated regions 116. The electrode assembly of FIG. 4A is configured to unilaterally stimulate both the supraorbital nerve and the infraorbital nerve. In other embodiments, the electrode assembly may comprise a plurality of multicontact electrodes which may include a plurality of contacts and a plurality of insulated regions. In various embodiments, the geometry or layout of the electrode assembly may be a linear electrode with a single contact or a series or plurality of conductive contacts and insulating spaces, or a flatter, "ribbon" or "strip" electrode, also with the possibility of one or more conductive area(s) and insulated area(s) on the surface(s). Those of skill in the art will recognize that other related geometries are also contemplated to be within the scope of the present disclosure.

As can be understood from FIG. 4A, in one embodiment, the electrode assembly may be implanted unilaterally. The electrode assembly may also be configured to stimulate more than one nerve. For example, as shown in FIG. 4A, the electrode assembly is configured to be placed at, near or over a plurality of superficial foramina in the face and simultaneously or asynchronously stimulate different trigeminal nerves (e.g. the supraorbital nerve and the infraorbital nerve).

Figure 4B:
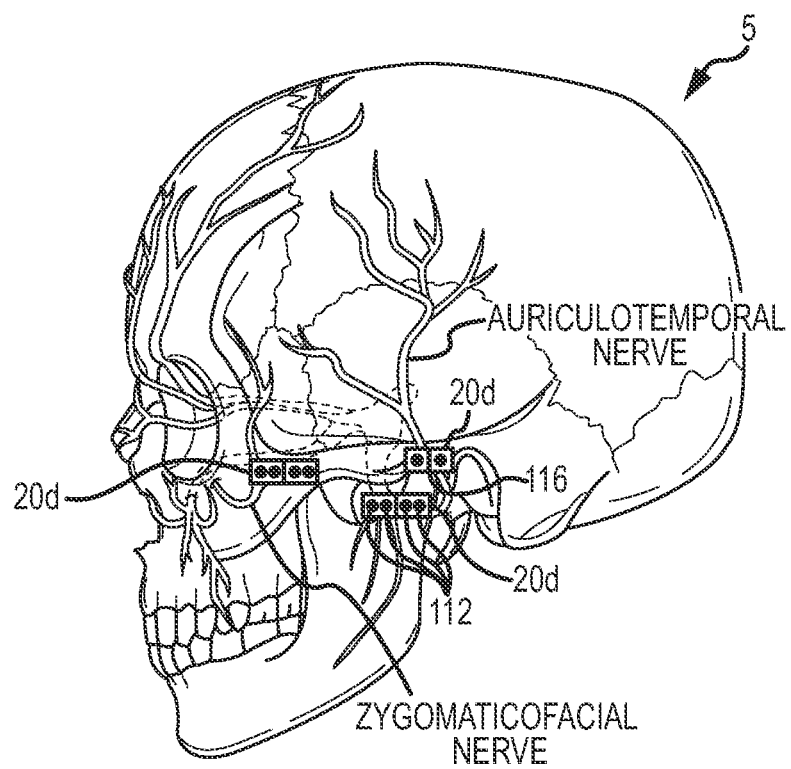
FIG. 4B depicts another embodiment of a subcutaneous electrode assembly configured for stimulation of the auriculotemporal or zygomaticofacial nerve branches which may be used with the system of FIG. 2A.

FIG. 4B depicts still another embodiment of an electrode assembly 20 that may be used in the system 200. In some embodiments, as shown in FIG. 4B, the electrode assembly 20 may comprise a multicontact electrode 20d with a plurality of contacts 112 and a plurality of insulated regions 116. The electrode assembly of FIG. 4B is configured to unilaterally stimulate at least one of the auriculotemporal nerve or the zygomaticofacial nerve. In other embodiments, the electrode assembly 20d may be configured to stimulate both the auriculotemporal nerve and the zygomaticofacial nerve. As can be understood from FIG. 4B, in one embodiment, the electrode assembly may be implanted unilaterally. The electrode assembly is configured to be placed at, near or over a superficial foramina in the face and simultaneously or asynchronously stimulate one or more different trigeminal nerves (e.g. the auriculotemporal nerve and/or the zygomaticofacial nerve).

Those skilled in the art will appreciate that various adaptations and modifications of the above-described embodiments of the electrode assembly 20 are within the scope and spirit of the present disclosure. For example, one embodiment of the present device comprises a unilateral electrode assembly configured for the unilateral stimulation of ophthalmic nerves (see FIGS. 4A-4B). In other embodiments, the implantable electrode assembly may be configured for the stimulation of the infraorbital nerves or the mentalis nerves. In other embodiments, the electrode assembly may be configured for the stimulation of the auriculotemporal nerve. In one embodiment, the electrode assembly may be configured for the stimulation of the zygomaticofacial nerve. In other embodiments, an electrode assembly may be configured for the simultaneous or asynchronous stimulation of a plurality of elements of the trigeminal nerves, either unilaterally or bilaterally. In other embodiments, both external, transcutaneous electrodes and implanted subcutaneouselectrodes are used to simultaneously or asynchronously stimulate one or more branches of the trigeminal nerves. The external, transcutaneous electrode assemblies are described in copending U.S. patent application Ser. No. 12/898,686.

For ease of the reader, the remaining discussion is made with respect to FIG. 2B. However, it is understood that the disclosure also applies to embodiments which include a single multicontact electrode with a plurality of contacts, a single contact electrode, and embodiments which include a plurality of multicontact electrodes with a plurality of contacts and embodiments configured for unilateral or bilateral stimulation and other embodiments within the spirit and scope of the present disclosure.

As can be understood from FIG. 2B, the electrode assembly 20 is configured to stimulate both the right and left ophthalmic nerves either simultaneously or asynchronously. The placement of the first implanted electrode with contact pair 112a, 112b and the second electrode with contact pair 112c, 112d on opposite sides of the nasal midline assures that stimulation current moves orthodromically or in the direction of the afferent ophthalmic or supraorbital nerve. Furthermore, this configuration of the electrode assembly 20 allows the electrode contact points 112a/112b and 112c/112d to be stimulated independently and/or unilaterally, as the response to stimulus may be localized and thus varied from one side of the midline to the other side. Depending on the location of the pulse generator, in some embodiments, the electrodes and/or their connectors (e.g. the wires 40) are longer than 150 mm where the supraorbital, infraorbital and/or the mentalis branch is the desired target. For other branches, a shorter electrode/connector length may be desired depending on the placement of the pulse generator.

For stimulations where electrical pulses of a single polarity are generated, the upper electrode contact points 112a, 112c and lower contact points 112b, 112d have fixed polarities. For stimulations where electrical pulses of alternating polarities are generated, the upper contact points 112a, 112c and lower contact points 112b, 112d have alternating polarities.

Each of the contacts 112a, 112b, 112c, 112d is configured to deliver an electrical pulse with minimal scalp tissue injury due to excess charge accumulation, and with minimal potential for current penetration beyond the inner surface of the skull bone. The distance between the first implanted electrode contact pair 112a, 112b and the second electrode contact pair 112c, 112d is configured to stimulate the ophthalmic nerves while minimizing any current delivery to the surface of the brain. The electrode size and the inter-electrode distance of electrode placement may vary for children and adults, males and females, depending upon the dimensions of an individual person's anatomy.

Electrode assembly 20, and in particular the contact points 112a, 112b, 112c, 112d, may be made of a noble or refractory metal or compound, such as titanium, titanium nitride, platinum, iridium, tantalum, niobium, rhenium, palladium, gold, nichrome, stainless steel, or alloys of any of these, in order to avoid corrosion or electrolysis which could damage the surrounding tissues and the device. Other compounds for implantable electrodes will be apparent to one skilled in the art.

In various embodiments, the distance between contacts 112a and 112b and the distance between contacts 112c and 112d can be in a range greater than, equal to, and/or less than one or more of 0.1 cm, 0.5 cm, 1 cm, 2 cm, 3 cm, 4 cm, 5 cm, 6 cm, 7 cm, 8 cm, 9 cm, or 10 cm. Those of skill in the art will recognize that one or more of the above distances can be used as a border of a range of distances.

Those skilled in the art will appreciate that various adaptations and modifications of the above-described embodiments of the electrode assembly 20 are within the scope and spirit of the present disclosure. For example, one embodiment of the present device comprises a unilateral electrode assembly configured for the unilateral stimulation of ophthalmic nerves. In other embodiments, the implantable electrode assembly may be configured for the stimulation of the infraorbital nerves or the mentalis nerves. In other embodiments, an electrode assembly may be configured for the simultaneous stimulation of a plurality of elements of the trigeminal nerves.

In some embodiments, both external, transcutaneous electrodes and implanted electrodes are used to simultaneously or asynchronously stimulate one or more branches of the trigeminal nerves.

In some embodiments, sensing electrodes are included in the electrode array to monitor physiological parameters, such as electroencephalographic data, and permit a feedback system that can adaptively adjust the stimulation parameters to optimize therapeutic benefit and safety. In some embodiments, the sensing electrode is one of the stimulating electrodes and is used for sensing during the 'off' part of the duty cycle. In some embodiments, the sensing electrode is an additional electrode and is dedicated to sensing only.

As can be best understood from FIGS. 2A-2B, the electrode assembly 20 is implanted in the soft tissues of the forehead of the patient 20. The electrode 20 is then connected to an implanted neurostimulator 30 via the implanted electrical cables 40, which are placed under the patient's skin. In the illustrated embodiment, the stimulation via the neurostimulator 30 is via electrical cables 40. In alternative embodiments, the electrical stimulation can be performed wirelessly, with an external, non-implanted neurostimulator, which uses inductive coupling to deliver energy to the implanted electrode assembly 20. The stimulation is carried out at the above-described values of the operational parameters. The values of the operational parameters are advantageously selected such that a patient will experience a stimulation sensation, such as mild tingling over the forehead and scalp, without causing the patient significant discomfort or pain and with minimal current penetration to the brain. These values may vary according to the treatment of interest.

The stimulation is carried out at the operational parameters as described herein. In some embodiments, the values of the operational parameters may be selected such that a patient will experience a stimulation sensation, such as mild tingling over the forehead, scalp, or teeth, without causing the patient significant discomfort or pain. These values may vary according to the treatment of interest.

According to one aspect of the present disclosure, there is provided a method of treatment of neuropsychiatric disorders using the electrode assembly 20, as described above. In one embodiment, the method of treating psychiatric disorders comprises implanting the electrode assembly 20 to the forehead of a patient, connecting the electrode assembly 20 to a neurostimulator 30, and stimulating the electrode assembly 20 at defined values of the operational parameters. In one embodiment, the bilateral supraorbital electrode 20 as disclosed herein is stimulated at a stimulus frequency between about 20 and about 300 Hz, at a pulse duration between 50 microseconds (µsec) to 250 µsec, at an output current of less than 10 mA for at least one-half to one hour per day. In some cases, stimulation can be provided for less than one-half hour per day or may be provided for up to 24 hours per day.

Accepted standards of safe stimulation may be incorporated for chronic stimulation. Parameters may be selected or calculated to deliver no stimulation or negligible stimulation to the surface of the brain. The currently accepted safe parameters for chronic stimulation are less than a charge per phase of <20 µC/cm$^2$/phase at the surface of the brain (Exp Neurol 1983; 79:397-41). In general, for any region of the surface of the brain, the cumulative charge per phase resulting from all the electrode contacts should not exceed this threshold. It is recognized that these guidelines are subject to change, and that parameters should be selected which deliver no current or negligible current to the surface of the brain, while still being sufficient to stimulate the nerves disclosed herein.

According to one aspect of the present disclosure, the method of treating neuropsychiatric disorders by TNS comprises selecting optimal values for the operational parameters for the stimulation of each individual patient. In one embodiment, the values of the operational parameters are selected such that a patient will experience a stimulation sensation, such as a mild tingling over the forehead, scalp, or face, without being in discomfort or in pain. In some embodiments, lower currents (e.g. 0.05-5 mA) and careful electrode placement may be selected to avoid recruitment of nerves supplying pain sensation to the teeth. In some embodiments, lower currents (e.g. 0.05-5 mA) may also be selected to avoid penetration of the current into the skull and brain, especially in supraorbital locations.

In one embodiment, the method of selecting operational parameters comprises evaluating variables such as the pulse duration, the electrode current, the duty cycle and the stimulation frequency; the parameters are selected to ensure that the total charge, the charge density, and charge per phase are well within accepted safety limits for the scalp or facial tissue, nerve and brain. Additionally, in some embodiments, selection of the electrical stimulation parameters, electrode design, and inter-electrode distance is made such that the electrical stimulation zone includes the superficial elements of the trigeminal nerves (approximately 3-4 mm deep), while preventing or minimizing current penetration beneath the bone tissue of the skull.

In various embodiments, the stimulation parameters delivered by the implanted pulse generator may be determined (programmed) at the time the device is surgically implanted. In other embodiments, these parameters may be modified, controlled, or otherwise programmed by an external device. This external programming element communicates with the implanted components wirelessly. This may take place, for example, by radiofrequency signals, by inductive coupling, or other means apparent to one skilled in the art.

In various embodiments, the stimulation is delivered at a specific pulse width or range of pulse widths. The stimulation can be set to deliver pulse widths in the range greater than and/or less than one or more of 50 µs, 60 µs, 70 µs, 80 µs, 90 µs, 100 µs, 125 µs, 150 µs, 175 µs, 200 µs, 225 µs, 250 µs, up to 500 µs. Those of skill in the art will recognized that one or more of the above times can be used as a border of a range of pulse widths.

In some embodiments, the stimulation amplitude is delivered as a voltage or current controlled stimulation. In other embodiments it can be delivered as a capacitive discharge. In various embodiments, the current amplitude can be in any range within a lower limit of about 300 µA and an upper limit of about 30 mA-35 mA, depending on the surface area of the electrodes, inter-electrode distance, the branch(es) stimulated, and the modeling data as described above. In some embodiments, the current used will range from 0.1 mA to 10 mA. In other embodiments, the current used will range from 0.1-3 mA. In various embodiments, the amplitude can be in a range greater than and/or less than one or more of 50 µA, 75 µA, 100 µA, 125 µA, 150 µA, 175 µA, 200 µA, 225 µA, 250 µA, 275 µA, 300 µA, 325 µA, 350 µA, 375 µA, 400 µA, 425 µA, 450 µA, 475 µA, 500 µA, 525 µA, 550 µA, 575 µA, 600 µA, 625 µA, 650 µA, 675 µA, 700 µA, 725 µA, 850 µA, 875 µA, 900 µA, 925 µA, 950 µA, 975 µA, 1 mA, 2 mA, 3 mA, 4 mA, 5 mA, 6 mA, 7 mA, 8 mA, 9 mA, 10 mA, 20 mA. Those of skill in the art will recognize that one or more of the above amplitudes can be used as a border of a range of amplitudes. The current may be delivered constantly or intermittently.

In some embodiments, treatment at a given current amplitude is delivered so as to minimize or eliminate any spread of current to the cerebral cortex, while ensuring that accepted limits of charge density and charge per phase at the brain surface (e.g., generally <20 µC/cm$^2$/phase, Exp Neurol 1983; 79:397-411) are adhered to, for the safety of the patient. Without wishing to be bound by any particular theory, it is believed that with the use of multicontact electrodes as described herein, even lower charge densities may be employed because more fibers within the nerves may be engaged in the neurostimulation process.

In various embodiments, the stimulation can be delivered at one or more frequencies, or within a range of frequencies. The stimulation can be set to be delivered at frequencies less than, and/or greater than one or more of 50 Hz, 45 Hz, 40 Hz, 35 Hz, 30 Hz, 25 Hz, 20 Hz, 15 Hz, or 10 Hz. In various embodiments, the stimulation can be set to be delivered at frequencies greater than, and/or less than, one or more of 20 Hz, 30 Hz, 40 Hz, 50 Hz, 60 Hz, 70 Hz, 80 Hz, 90 Hz, 100 Hz, 125 Hz, 150 Hz, up to 300 Hz. Those of skill in the art will recognize that one or more of the above frequencies can be used as a border of a range of frequencies.

In various embodiments, the stimulation is delivered at a specific duty cycle or range of duty cycles. The stimulation can be set to be delivered at a duty cycle in the range greater than and/or less than one or more of 5%, 10%, 15%, 20%, 25%, 30%, 35%, 40%, 45%, 50%, 55%, 60%, 65%, 70%, 75%, 80%, 85%, 90%, 95%, or 100%. In some embodiments, to ensure preservation of the nerve, a duty cycle of 10% to 50% may be preferable. In some embodiments, duty cycles up to 100% may be useful in particular circumstances. Those of skill in the art will recognized that one or more of the above percentages can be used as a border of a range of duty cycles.

According to one aspect of the present disclosure, the method of treating psychiatric disorders by TNS comprises selecting optimal values for the operational parameters for the stimulation of each individual patient. In one embodiment, the values of the operational parameters are selected such that a patient will experience a stimulation sensation, such as a mild tingling over the forehead, scalp, or face without being in discomfort or in pain. In some embodiments, lower currents and careful electrode placement may be selected to avoid recruitment of nerves supplying pain sensation to the teeth. In some embodiments, lower currents may also be selected to avoid penetration of the current into the skull and brain, especially in supraorbital locations. In some embodiments, the neurostimulation parameters are important factors in the treatment method. In one embodiment, the method of selecting operational parameters comprises evaluating variables such as the pulse duration, the electrode current, the duty cycle and the stimulation frequency; the parameters are selected to ensure that the total charge, the charge density, and charge per phase are well within accepted safety limits for the scalp or facial tissue, nerve and brain. Additionally, in some embodiments, selection of the electrical stimulation parameters, electrode design, and inter-electrode distance is made such that the electrical stimulation zone includes the superficial elements of the trigeminal nerves (approximately 3-4 mm deep), while preventing or minimizing current penetration beneath the skull bone.

In various embodiments, the stimulation parameters delivered by the implanted neurostimulator may be determined (programmed) at the time the device is surgically implanted. In other embodiments, these parameters may be modified, controlled, or otherwise programmed by an external device. This external programming element communicates with the implanted components wirelessly. This may take place, for example, by radiofrequency signals, by inductive coupling, or other means apparent to one skilled in the art.

In some embodiments, an external device may be used to identify the location of the branch or branches of the trigeminal nerve that will be targeted in an individual patient for stimulation by the implanted electrode assembly disclosed herein. The external device may be used for mapping and targeting the desired branch or branches of the trigeminal nerve and for identifying the individual stimulation parameters that are optimal for efficacy and safety. In one embodiment, the device may include a plurality of external (transcutaneous) TNS electrodes. The practitioner approximates the location of the target branch and affixes the electrodes to the patient's skin above the target location. Stimulation may be applied and the actual location or preferred (optimal) stimulation location of the target branch or branches may be determined. Stimulation parameters may also be established. Once the location and/or stimulation parameters have been established via the external device, that data may be used to help guide the placement of the implanted electrodes for an individual patient and to establish the customized stimulation parameters for that patient.

In addition, the use of external electrodes for stimulation of the trigeminal nerve may identify individuals who are likely to derive therapeutic benefit from this minimally invasive system in addition to the optimal specific locations and parameters of stimulation based on person-to-person variability. Various neurodiagnostic, imaging, or cutaneous nerve mapping methods may be able to delineate differences in individual anatomy to optimize stimulation for efficacy and/or safety. Furthermore, the use of this minimally invasive system may allow screening and identification of those individuals who are likely to derive benefit from other implantable systems, such as deep brain stimulation. This can be conceptualized as linking the three approaches as stage I (external TNS of the trigeminal nerve), stage II (implanted TNS of the superficial trigeminal nerve), and stage III (deep brain stimulation), such that stage I can screen for stage II, and stage II for stage III. By monitoring a patient for evidence of useful therapeutic effect, such as by reduction in the severity of symptoms, the results of treatment at one stage may be used to judge the likely effect of treatment with a more invasive treatment from a higher stage.

A method of evaluating the use of trigeminal nerve stimulation for treatment of a neurological disorder in a patient is disclosed herein. The method may include applying a transcutaneous system for stimulation of the trigeminal nerve to the patient and monitoring the patient for at least one of evidence of a useful therapeutic response or evidence of tolerability of TNS treatment, providing a subcutaneous electrode assembly or system as disclosed herein, and implanting the subcutaneous electrode assembly or system as disclosed herein in the patient for treatment of a neurological disorder.

A method of evaluating the use of deep brain stimulation for treatment of a neurological disorder in a patient is disclosed herein. The method may include applying a transcutaneous system for stimulation of the trigeminal nerve to the patient and monitoring the patient for at least one of evidence of a useful therapeutic response or evidence of tolerability of TNS treatment thereby generating external measurement criteria, providing a subcutaneous electrode assembly or system as disclosed herein, implanting the subcutaneous electrode assembly or system as disclosed herein in the patient for treatment of a neurological disorder, monitoring the patient for at least one of a useful therapeutic response or tolerability of the implanted device, thereby generating extracranial measurement criteria, and analyzing the external measurement criteria and extracranial measurement criteria to determine whether the patient will benefit from deep brain stimulation.

The following examples are presented to set forth more clearly the subject matter of this disclosure without imposing any limits on the scope thereof and to illustrate the clinical benefits of trigeminal nerve stimulation for the treatment of neuropsychiatric disorders. In the first example, patients with major depressive disorder were treated by TNS with external transcutaneous electrodes. In the second example, a patient was treated using transcutaneous electrodes for bilateral supraorbital stimulation.

EXAMPLE 1

Figures 5A, 5B:
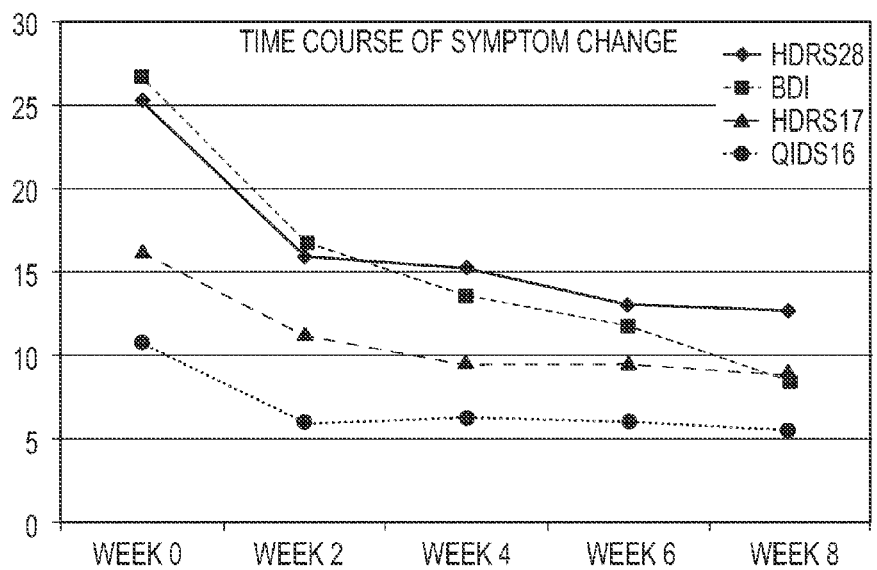
FIG. 5A is a table showing an average of the results of four assessment tests pre-treatment and post treatment of a treatment study for psychiatric disorders using aspects of the present disclosure.
FIG. 5B is a bar graph of the data shown in FIG. 5A.
Figure 5C:
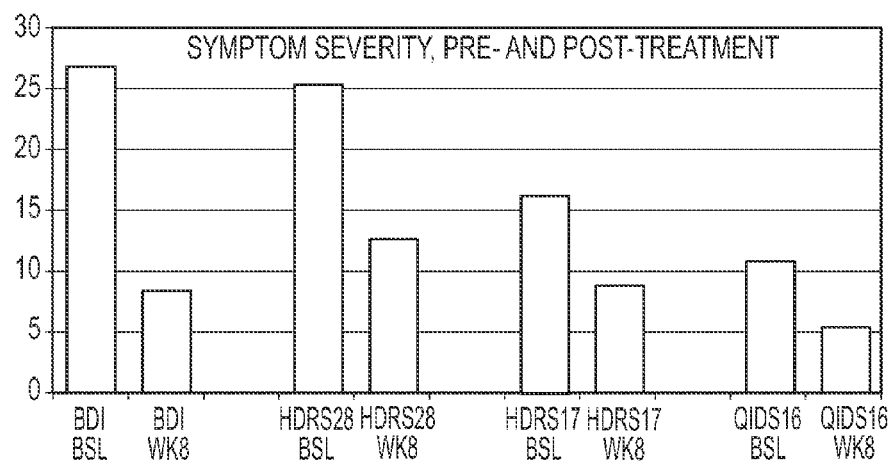
FIG. 5C is a graph illustrating the change over time of the data shown in FIG. 5A.

FIGS. 5A-5C illustrate the results from a pilot study of external trigeminal nerve stimulation for the treatment of depression. Subjects with major depression who met inclusion and exclusion criteria were followed for 8-weeks in an open label (unblinded) study conducted at UCLA.

Inclusion Criteria were: Age 18-65 years old who met DSM-IV criteria for an acute, recurrent episode of Major Depressive Disorder (MDD) and were in a major depressive episode (MDE) of moderate severity. Other inclusion criteria were: the current MDE must be ≥4 months in duration, no response to at least one antidepressant over at least six weeks during the current MDE, and concomitant use of at least one antidepressant. All had prominent residual symptoms, with mean Hamilton Depression Rating Scale (HDRS-28) scores at study entry of 25.4 (3.9 s.d.), range 19 to 29. Subjects placed stimulating electrodes over the supraorbital branches of the trigeminal nerve for at least 8 hours per day (primarily while asleep), with current adjusted to maintain comfortable levels. Five subjects completed the trial. Primary outcome was change in HDRS at 8 weeks.

Exclusion criteria were: current pregnancy; meeting DSM-IV criteria for atypical or psychotic or bipolar depression; a history of schizophrenia, schizoaffective disorder, or other non-mood disorder psychosis; a current secondary DSM-IV diagnosis (or signs) of delirium, dementia, amnestic disorder or other cognitive disorder; clinically significant current suicidal intent; significant cardiac, medical or progressive neurological or medical illness; facial pain or trigeminal neuralgia; a VNS or other implantable electrical device such as a pacemaker; current use of a TENS or VNS unit, or history of non-compliance.

All subjects received unblinded TNS augmentation (adjunctive) treatment for at least 8-hours each day. Assessments were made at study intake, and at weeks 2, 4, 6, and 8 in the acute treatment phase. Subjects who wished to continue the treatment were allowed to participate in an optional 6-month long-term extension phase with monthly monitoring visits.

Subjects underwent stimulation using an electrical stimulator, such as for example the EMS Model 7500 commercially available from TENS Products, Inc. (www.tensproducts.com) operated at a frequency of 120 Hertz, a current less than 20 mA, a pulse duration of 250 μsec, and a duty cycle at 30 seconds on and 30 seconds off, for a minimum of 8 hours per day.

Prior to initiating treatment and at subsequent follow-up assessment visits, the symptom severity of each subject was quantified using the Hamilton Depression Rating Scale (HDRS, scored using both 17- and 28-item versions), the Beck Depression Inventory (BDI), and the Quick Inventory of Depressive Symptomatology (QIDS), with the group average values on each of these scales being tabulated in the table shown in FIG. 5A. All three are assessment instruments designed to measure the severity of depression. The HDRS is a well-established rating scale instrument which is filled out by a clinician after interviewing and observing the individual subject in order to measure the severity of depression; in this study, ratings on all 28 items (questions) were made, and the scale was scored according to standard methods using all items ($HDRS_{28}$) and the standard subset of 17 items ($HDRS_{17}$). The BDI is a 21-question multiple choice self-report survey that is used to measure the severity of depression. The $QIDS-C_{16}$ is a 16-question clinician-rated survey that is used to measure the severity of depression. Each of these scales affords different strengths and limitations in assessing a patient's symptom severity (e.g. BDI emphasizes cognitive symptoms of depression, while the HDRS weights neurovegetative symptoms prominently), and all are commonly used in clinical trials in major depression; the use of multiple scales allowed a more comprehensive assessment of the effects of trigeminal nerve stimulation than any single scale in this initial study of this treatment for major depression.

As shown in FIG. 5A, and graphically illustrated in FIGS. 5B and 5C, decreases in $HDRS_{28}$ were significant, from 25.4 (3.9 s.d.) at entry to 13.6 (6.3 s.d.) at week 8 (2-tail t-test $p<0.01$, Cohen's d 2.4). Responses on the BDI similarly declined, from 26.8 (8.1) to 10.6 (4.9) ($p<0.01$, d 2.3). Decreases on the 16-item clinician-rated QIDS were also significant, decreasing from 10.8 (3.4) to 5.5 (4.4) ($p<0.05$, d 1.3). Thus, significant decreases in symptom severity were achieved in the 8 weeks of acute TNS treatment. Furthermore, changes in symptoms occurred across all symptom areas, such as depressed mood, anxiety, sleep, and energy. These findings support the use of TNS treatment which may also have use as an adjunct to pharmacotherapy when medications have failed to produce remission of symptoms.

EXAMPLE 2

FIG. 6 summarizes current, charge, current density and charge density recorded in a subject during exposure to transcutaneous stimulation of the supraorbital nerve. FIG. 6 illustrates representative parameters for bilateral supraorbital stimulation recorded in a subject using an EMS 7500 stimulator, 120 HZ, 150-250 usec, Tyco superior silver electrodes 1.25", one inch from the midline above the eyebrows. Data recorded with Fluke Oscilloscope, 50 mV/div, resistor=10.1Ω. In general, these finding show that as the pulse width increased, the maximum tolerable current decreased.

Transcutaneous electrical stimulation of the supraorbital branch of the trigeminal nerve with round 1.25-inch TENS patch electrodes results in current densities and charge density/phase that are well within the limits of safety. In general, the maximum current comfortably tolerated by TNS patients studied previously is approximately 25 mA's, and patients typically are stimulated at an amplitude setting well below 25 mA's (6-10 mA's).

The 1.25-inch TENS electrodes are circular electrodes with a radius of 1.59 cm. The surface area can be calculated as $A=\Pi r^2=[\Pi]\times[1.59 \text{ cm}]^2=7.92 \text{ cm}^2$. Using these electrodes, typical stimulation current ranges from 6-10 mA at pulse durations of 150-250 usec.

Current Density: In a typical subject, stimulation currents of 6-10 mA result in current densities ranging from 0.76 to 1.3 $mA/cm^2$. McCreery et al have established a maximum safe current density of 25 mA/cm at the stimulating electrode for transcranial electrical stimulation. Assuming even higher currents of up to 25 mA with electrodes of surface area 7.92 $cm^2$, current densities may range to a maximum of 3.16 $mA/cm^2$. From 0.76 $mA/cm^2$ to 3.16 $mA/cm^2$, TNS delivers a current density 8-33 times less than the maximum safe allowable current density. Charge Density (Charge density/phase): Yuen et al have identified a safe limit for charge density/phase delivered at the cerebral cortex of 40 $uC/cm^2$. [Yuen et al 1981] Assuming 10 mA at 250 usec, the charge density/phase is $[0.010 A]\times[250 \text{ usec}]/7.92=0.32 \text{ uC/cm}^2$ at the stimulating electrode. Assuming even higher levels of stimulation, 25 mA at 250 usec, the maximum charge density per phase is 0.79 $uC/cm^2$. At these levels, the charge density is generally 50 to 260 fold less at the stimulating electrode than the maximum allowed at the cerebral cortex. Since the cortex is a minimum of 10-13 mm from the stimulating electrodes, and given the layers of skin, fat, bone, dura, and CSF, the actual charge densities will be significantly lower.

As shown in FIG. 6, stimulation intensity responses in a subject with electrodes of surface area 7.92 cm2, at pulse durations between 150-250 usec, results in current densities at the scalp well below currently recommended current densities for transcranial stimulation, which are 25 mA/cm², and charge densities at the scalp significantly lower than safe charge densities at the cerebral cortex (0.15-0.18 uC/cm²).

From the foregoing discussion, it will be appreciated that the invention can be embodied in various ways which include, but which are not limited to, the following:

1. A method of treating a neuropsychiatric disorder in a patient having a trigeminal nerve, the method comprising: implanting at least one electrode in the patient in proximity to at least one superficial branch of the trigeminal nerve; and applying adjustable electric signals to at least one superficial branch of the trigeminal nerve through the at least one electrode.

2. The method of embodiment 1, wherein the at least one superficial branch of the trigeminal nerve is a supraorbital nerve.

3. The method of embodiment 1, wherein the at least one superficial branch of the trigeminal nerve is a infraorbital nerve.

4. The method of embodiment 1, wherein the at least one superficial branch of the trigeminal nerve is a mentalis nerve.

5. The method of embodiment claim 1, wherein the step of applying adjustable electric signals comprises applying electrical signals at a frequency of about 20 to 300 Hertz, at a constant current of 0.05 to 20 milliamperes (mA), and a pulse duration of less than or equal to 500 microseconds.

6. The method of embodiment 1, wherein the step of applying adjustable electrical signals comprises applying electrical signals for less than 12 hours per day.

7. An implantable device for stimulation of a superficial branch of a trigeminal nerve, the device comprising: at least two electrodes, each electrode having an upper contact point and a lower contact point, and each electrode configured to be placed adjacent to a superficial branch of a trigeminal nerve; and means for connecting the at least two electrodes to an implanted neurostimulator; wherein adjustable electrical signals generated by the implanted neurostimulator are transmitted to a superficial branch of the trigeminal nerve via the at least two electrodes.

8. A method of treating a neuropsychiatric disorder in a patient, the method comprising: providing a device provided in accordance with embodiment 7; implanting the device in the patient such that the at least two electrodes are placed adjacent to a superficial branch of the trigeminal nerve; and applying an electric current to the device of between 0.05 and 20 milliamperes, with a frequency of between 20 and 300 Hertz with a pulse duration not exceeding 500 microseconds.

1. A subcutaneous electrode assembly for trigeminal nerve stimulation, the subcutaneous electrode assembly comprising: a first electrode comprising a first pair of contacts configured for subcutaneous placement at a first region of a patient's face; and a second electrode comprising a second pair of contacts configured for subcutaneous placement at a second region of a patient's face; wherein the first pair of contacts and the second pair of contacts are configured to be bilaterally implanted in proximity to, adjacent to or in contact with at least one branch of the trigeminal nerve for treatment of a neuropsychiatric disorder by trigeminal nerve stimulation.

2. The subcutaneous electrode assembly of claim 1, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, and auriculotemporal nerve.

3. A subcutaneous electrode assembly for trigeminal nerve stimulation, the subcutaneous electrode assembly comprising: a first electrode comprising a first plurality of contacts configured for subcutaneous placement at a first region of a patient's face; and a second electrode comprising a second plurality of contacts configured for subcutaneous placement at a second region of a patient's face; wherein the first plurality of contacts and the second plurality of contacts are configured to be unilaterally implanted in proximity to, adjacent to or in contact with at least two different branches of the trigeminal nerve for treatment of a neuropsychiatric disorder by trigeminal nerve stimulation.

4. The subcutaneous electrode assembly of claim 3, wherein the at least two different branches of the trigeminal nerve are selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, and auriculotemporal nerve.

5. A method for treating a neuropsychiatric disorder or condition by trigeminal nerve stimulation, comprising: implanting an electrode assembly in a patient, the subcutaneous electrode assembly comprising: a first electrode comprising a first plurality of contacts configured for subcutaneous placement at a first region of the patient's face; a second electrode comprising a second plurality of contacts configured for subcutaneous placement at a second region of the patient's face, wherein the first plurality of contacts and the second plurality of contacts are configured to be implanted in proximity to, adjacent to or in contact with at least one branch of the trigeminal nerve; and applying electrical signals to the electrode assembly at specified operational parameters to treat a neuropsychiatric disorder.

6. The method of claim 5, wherein the step of applying electrical signals comprises applying electrical signals at a frequency between approximately 20 and 300 Hertz, at a current of 0.05 to 5 milliamperes (mA) and at a pulse duration of less than or equal to 500 microseconds.

7. The method of claim 5, wherein the step of applying electrical signals comprises applying electrical signals at a frequency between approximately 20 and 300 Hertz, at a current of 0.05 to 2 milliamperes (mA) and at a pulse duration not exceeding 500 microseconds.

8. The method of claim 5, wherein the neuropsychiatric disorder is depression.

9. A system for trigeminal nerve stimulation for treatment of a neuropsychiatric disorder, the system comprising: a pulse generator; and a subcutaneous electrode assembly comprising: a first electrode comprising a first plurality of contacts configured for subcutaneous placement at a first region of the patient's face; and a second electrode comprising a second plurality of contacts configured for subcutaneous placement at a second region of the patient's face, wherein the first plurality of contacts and the second plurality of contacts are configured to be implanted in proximity to, adjacent to or in contact with at least one branch of the trigeminal nerve 10. The system of claim 9 further comprising a wire operably connecting the pulse generator and the subcutaneous electrode assembly.

11. The system of claim 9, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, and auriculotemporal nerve.

12. A kit for trigeminal nerve stimulation for treatment of a neuropsychiatric disorder, the kit comprising: the subcutaneous electrode assembly according to claim 1; and instructions for implanting the electrode assembly in a patient for treatment of a neuropsychiatric disorder or condition.

13. The kit of claim 12, further comprising: a pulse generator; and instructions for applying electrical signals to the electrode assembly for treatment of a neuropsychiatric disorder or condition.

14. A kit for trigeminal nerve stimulation for treatment of a neuropsychiatric disorder, the kit comprising: the subcutaneous electrode assembly according to claim 3; and instructions for implanting the electrode assembly in a patient for treatment of a neuropsychiatric disorder.

15. The kit of claim 14, further comprising: a pulse generator; and instructions for applying electrical signals to the electrode assembly for treatment of a neuropsychiatric disorder.

16. A subcutaneous electrode assembly for trigeminal nerve stimulation, the subcutaneous electrode assembly comprising: a first electrode comprising a first single contact configured for subcutaneous placement at a first region of a patient's face; and a second electrode comprising a second single contact configured for subcutaneous placement at a second region of a patient's face; wherein the first contact and the second contact are configured to be implanted in proximity to, adjacent to or in contact with at least one branch of the trigeminal nerve for treatment of a neuropsychiatric disorder by trigeminal nerve stimulation.

17. The subcutaneous electrode assembly of claim 16, wherein the at least one branch of the trigeminal nerve is selected from the group consisting of: ophthalmic nerve, infraorbital nerve, mentalis nerve, supratrochlear nerve, infratrochlear nerve, zygomaticotemporal nerve, zygomaticofacial nerve, zygomaticoorbital nerve, and auriculotemporal nerve.

Those skilled in the art will appreciate that various adaptations and modifications of the above described preferred embodiments may be configured without departing from the scope and spirit of this disclosure. Stimulation of the target nerve may be accomplished by application of energy in many forms, such as magnetic or ultrasonic. Therefore, it is to be understood that the subject matter of this disclosure may be practiced other than as specifically described herein.

What is claimed is:

1. A method for treating a neuropsychiatric disorder by trigeminal nerve stimulation, comprising:
    implanting a subcutaneous electrode assembly in a patient so that a first electrode contact is in contact with a supraorbital nerve on one side of a patient's forehead and so that a second electrode contact is in contact with a supraorbital nerve on an opposing side of the patient's forehead; and
    applying electrical signals to the electrode assembly so that current flows between the first electrode contact and the second electrode contact at specified operational parameters to treat the neuropsychiatric disorder, wherein the electrical signals are applied to minimize current penetration into a brain for the patient such that a charge density at the brain's surface does not exceed 20 $\mu C/cm^2$.

2. The method of claim 1, wherein the step of applying electrical signals comprises applying electrical signals at a frequency between approximately 20 and 300 Hertz, at a current of 0.1 to 3 milliamperes (mA) and at a pulse duration of less than or equal to 500 microseconds.

3. The method of claim 1, wherein the step of applying electrical signals comprises applying electrical signals at a frequency between approximately 20 and 300 Hertz, at a pulse duration between approximately 50 and 500 microseconds, at an output current density of not greater than approximately 25 $mA/cm^2$ and a charge density of not greater than approximately 10 $microCoulomb/cm^2$ at the cerebral cortex.

4. The method of claim 1, wherein the neuropsychiatric disorder is selected from the group consisting of: mood disorder, cognitive disorder, behavioral disorder and anxiety disorder.

* * * * *